United States Patent [19]

Jacobsen et al.

[11] 4,166,457

[45] Sep. 4, 1979

[54] FLUID SELF-SEALING BIOELECTRODE

[75] Inventors: Stephen C. Jacobsen; Robert L. Stephen; Richard D. Luntz; Richard T. Johnson; David F. Knutti; Carl F. Mandleco, all of Salt Lake City, Utah

[73] Assignee: University of Utah Research Institute, Salt Lake City, Utah

[21] Appl. No.: 851,082

[22] Filed: Nov. 14, 1977

Related U.S. Application Data

[63] Continuation-in-part of Ser. No. 714,942, Aug. 16, 1976.

[51] Int. Cl.² ............................................. A61B 5/04
[52] U.S. Cl. ..................................... 128/639; 128/803; 128/172.1
[58] Field of Search .............. 128/2.06 E, 2.1 E, 404, 128/410, 411, 416–418, DIG. 4

[56] References Cited

U.S. PATENT DOCUMENTS

| 3,187,745 | 6/1965 | Baum et al. | 128/2.06 E |
| 3,249,103 | 5/1966 | Woodhouse | 128/2.1 E |
| 3,580,240 | 5/1971 | Cosentino | 128/2.06 E |
| 3,610,229 | 10/1971 | Zenkich | 128/2.06 E |
| 3,862,633 | 6/1975 | Allison et al. | 128/2.06 E |
| 3,882,853 | 5/1975 | Gofman | 128/2.06 E |
| 4,040,412 | 8/1977 | Sato | 128/2.06 E |

FOREIGN PATENT DOCUMENTS 176033 12/1965 U.S.S.R. .................................. 128/417

Primary Examiner—Lee S. Cohen
Attorney, Agent, or Firm—Criddle, Thorpe & Western

[57] ABSTRACT

A dry-state bioelectrode having a self-sealing receptacle for receiving electrolyte and/or medicament fluid contents. The receptacle is attached at its opening to a sheet-like flexible base member having an opening in common with the receptacle opening, the bottom of the base member being adapted for fixation at a skin surface. A portion of the skin surface is exposed to the fluid contents of the receptacle through the common opening. An injection site communicates through the wall of the receptacle and provides controlled access for filling. Upon completion of filling, the receptacle self seals, retaining the fluid contents therein for application of iontophoresis treatment or other procedures requiring use of a potential gradient. An electrode plate is supported at an interior surface of the receptacle for supplying the desired electric potential.

16 Claims, 7 Drawing Figures

FLUID SELF-SEALING BIOELECTRODE

This is a Continuation-In-Part patent application of Parent Case Ser. No. 714,942, entitled "Epidermal Iontophoresis Device" filed Aug. 16, 1976.

BACKGROUND OF THE INVENTION

1. Field of the Invention

The subject invention relates to bioelectrodes utilizing a fluid electrolyte medium. More particularly, the present invention relates to bioelectrodes which are attached at a skin surface and are utilized for applying or measuring current or potential.

2. Prior Art

The field of bioelectrodes which are attachable at a skin surface and rely on electrolyte fluids to establish electrical contact with such skin surfaces can be divided into at least two categories. The first category includes those bioelectrodes which are prepackaged with the electrolyte contained in the electrode cavity or receptacle. The second type of bioelectrode is a dry-state electrode whose receptacle is customarily filled with electrolyte immediately prior to application to a skin surface. With both types of electrodes, the user currently experiences numerous problems which make their use both inconvenient and problematic.

With respect to the prepackaged electrode, storage is a major concern. Frequently, leakage of contents from the receptacle occurs, resulting in an inoperative or defective state. Furthermore, such prefilled electrodes are difficult to apply because the protective seal which covers the electrode opening and retains the fluid within the receptacle cavity must be removed prior to application to the skin surface. After removal of this protective seal, spillage often occurs in attempting to place the electrode at the skin surface. Such spillage impairs the desired adhesive contact of the electrode to skin surface and also voids a portion of the receptacle cavity. The consequent loss of electrolyte fluid tends to disrupt electrical contact with the electrode plate contained therein and otherwise disrupts the preferred uniform potential gradient to be applied.

Although dry-state electrodes have numerous advantages in ease of storage and greater adaptability for various types of electrode applications, several problems remain. For example, the electrolyte receptacles of such electrodes are conventionally filled through their opening prior to application to the patient's skin surface. Therefore, the same problem of spillage and loss of electrolyte upon application occurs as with the prefilled electrode.

Frequently, such electrodes are not well structured to develop the proper uniform current flow required in iontophoresis applications. Such nonuniform current flow may result from improper spacial relationship between the exposed skin surface and electrode plate, as well as from the occurrence of air pockets within the receptacle cavity. This effect occurs because of the nonuniform impedance associated with such air pockets, thereby disrupting the electric field and current path established between the electrode and exposed skin surface. Such effects are particularly troublesome in iontophoresis applications, where the induction of medicaments (such as anesthetic) relies upon the amount of current flow at any given point at the skin surface. Therefore, a nonuniform current flow results in unequal distribution of anesthetic through the skin surface, along with increased risk of burns. Previous methods of filling dry-state electrodes have not attempted to remedy the disrupted influence of such air pockets within the electrode cavity or the spillage problem of conventional filling techniques.

OBJECTS AND SUMMARY OF THE INVENTION

It is an object of the present invention to provide an electrode having self-sealing injection means for passing fluid contents into the electrode receptacle through an entry site other than the electrode opening.

It is also an object of this invention to provide a unibody electrode-fluid reservoir in which the fluid contents are prepackaged in a reservoir separate from the electrode receptacle but connected thereto by a self-sealing channel for subsequent filling procedures.

It is an object of the present invention to provide a dry-state electrode which remains substantially void of air during storage and subsequent filling with fluid, thereby reducing adverse effects of air pockets during application.

It is an additional object of the present invention to provide a bioelectrode which avoids the leakage and spillage associated with application of prefilled electrodes.

It is a further object of the present invention to provide a dry-state bioelectrode adapted for use to numerous forms of treatment or electrical monitoring, such as iontophoresis applications, EKG, EEG, etc.

It is yet another object of this invention to provide a bioelectrode which precludes localized physical contact between the electrode plate and exposed skin surface subject to the electrode treatment.

A further object of this invention is to provide a bioelectrode in combination with a reservoir means for filling such dry-state electrodes while attached at the skin surface to be treated.

A still further object of this invention is to provide an improved sealed electrode receptacle to prevent leakage of contained electrolyte.

A further specific object of this invention is to adapt such a dry-state electrode with means for limiting spillage upon removal of such electrode from the attached skin surface.

These objects are realized in a bioelectrode having self-sealing injection channel means which permits introduction of fluids, but automatically seals to preclude adverse leakage upon completion of filling. It is further adapted such that fluid introduction is not accompanied by air which develops adverse effects within the electrode during operating procedures. The basic structure of the self-sealing bioelectrode comprises a sheet-like base member having an opening therethrough, a receptacle attached to and having its opening in common with the opening of the base member. The receptacle may be made of deformable material for flattening against the base member to reduce the amount of air content within its structure. An injection channel is located to communicate between an exterior fluid reservoir which contains the desired electrolyte and the interior of the electrode receptacle. The injection channel includes a restricted access means for enabling self-sealing and blocking air passage during injection of fluid. An electrode plate is disposed within the cavity of the receptacle to provide current or other electric field influence for effecting the desired treatment or procedure.

DETAILED DESCRIPTION OF THE DRAWINGS

DETAILED DESCRIPTION OF PREFERRED EMBODIMENTS

Figure 1:
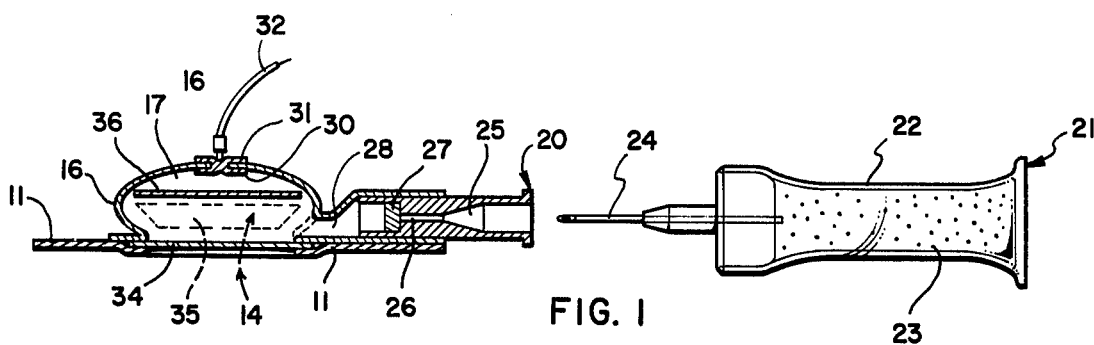
FIG. 1 shows a cross section, side view of a self-sealing bioelectrode with separate reservoir means.
Figure 2:
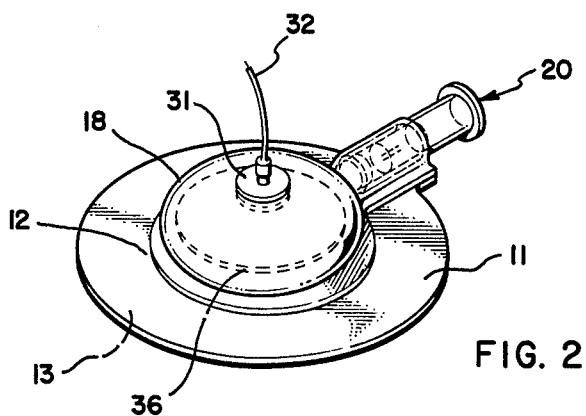
FIG. 2 is a perspective top view of the subject self-sealing electrode without the reservoir means.
Figure 3:
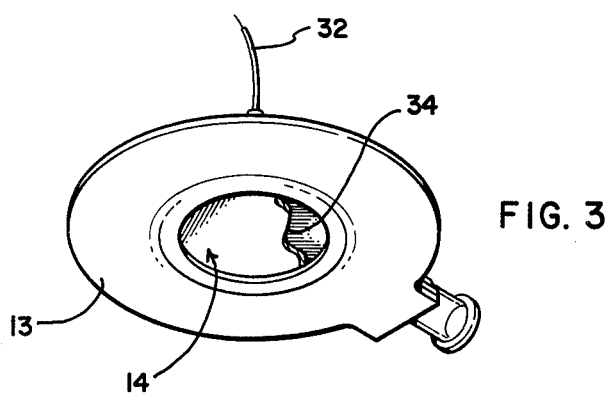
FIG. 3 is a partially cut away, perspective bottom view of the same bioelectrode as illustrated in FIGS. 1 and 2.

Referring now to the figures:

A self-sealing bioelectrode is represented by the embodiment illustrated and includes a sheet-like base member 11 which has a top surface 12 for supporting additional component members and a bottom surface 13 for fixation at a skin surface to be subjected to a particular electrical current application or monitoring procedure.

Exposure of the skin surface to be treated occurs through an opening 14 through the base member 11. Typically, the surface area of the skin subject to treatment will correspond with the area of the opening 14 and can therefore be controlled by modifying the size and shape of such opening to suit the particular purposes of treatment. For example, the shape of the base opening 14 may be elongate where an elongate area of skin is desired to be treated or otherwise monitored.

The base member 11 may be constructed of numerous materials; however, polyurethane and similar flexible materials are particularly well suited for use with the electrode. The flexibility provided by such polymer material incorporates conformable properties to the electrode which facilitate emplacement over contoured or swollen skin surfaces, fingers and other anatomical structures. Such materials are also more adaptable for trimming which may be required to locate the electrode adjacent to an ear, nose or other protrusion.

A receptacle 16 extends from the top surface 12 of the base member 11 and encloses a cavity, except for an opening which communicates in common with the base opening 14. These combined openings operate to expose contained fluid contents to the treated skin surface. The remaining receptacle-base interface is sealed to prevent leakage.

Figure 4:
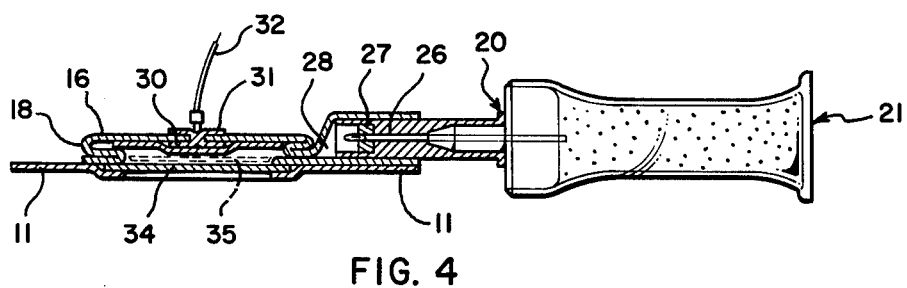
FIG. 4 shows the bioelectrode in a flattened state, with the reservoir means inserted at the injection channel means.

Inasmuch as a primary purpose of one embodiment of the present invention is to provide a substantially air-free bioelectrode cavity 17, the receptacle body 16 may be initially flattened against the base member 11 as illustrated in FIG. 4, minimizing air content during dry-state storage. Crease lines 18 may be included to reduce wrinkling and improve the extent of flattening and reduction of air pockets within the cavity area 17. The use of such marks also improves ease of extension of the receptacle upon charging with electrolyte.

It is apparent that the size of the receptacle member 16 will depend upon the nature of treatment or procedure to be utilized, as well as general factors of location of skin surface affected, base opening size, and type of fluid constitution. For iontophoresis applications of medication or anesthetic, for example, a uniform current flow is desired through the common base/receptacle opening 14. This uniform field is more easily obtained when the current source electrode is remote from the opening. By elongating the receptacle, such a current source can be located at the more distal end, increasing the distance from the opening 14.

Selection of materials for construction of the receptacle may be from numerous flexible plastics and other similar materials which permit deformation and subsequent fluid inflation in the respective dry and filled states. Here again, biocompatibility of material is preferable, as well as chemical compatibility with the anticipated electrolyte to be contained therein.

Filling of the receptacle 16 is accomplished at an injection channel means, shown generally as 20. The purpose of the injection channel means is to provide controlled access for fluid entry, while precluding introduction of air into the electrode cavity 17. The exclusion of air during the charging process is important, particularly in iontophoresis applications, because air pockets within the cavity 17 tend to disrupt the uniform field which is desired when applying certain medications such as anesthesia.

It is apparent that numerous forms of flow channels to the interior of the receptacle can operate as the injection channel means when such channels are blocked by a restricted access means. As used herein, restricted access means includes any device which is self-sealing with respect to an appropriate fluid filling procedure. Such access means will block fluid flow through the channel means, except as to such fluids as may be intentionally injected therethrough. A suitable restricted access means may simply comprise a self-sealing plug which closes upon withdrawal of an inserted syringe means, or it may comprise a one way valve or tube sealing system, the latter being illustrated in FIGS. 5–7.

FIGS. 1 and 4 illustrate the use of a reservoir means, such as a SYRETTE (Trademark) 21. The SYRETTE comprises deformable wall structure 22 for containing a desired electrolyte within a cavity 23 for ejection through a cannula means 24. Such a SYRETTE can be used to withdraw electrolyte (including iontophoresic medications) from a separate storage reservoir and transfer the amount withdrawn through the injection channel means 20 to the electrode cavity 17.

FIGS. 1–4 illustrate a two-stage injection channel means in which the cannula means 24 may be partially inserted into the first stage 26, represented by a narrow duct having an inner diameter corresponding to the outer diameter of the cannula means to provide a snug fit therein. The duct terminates at the second stage 27, comprising a self-sealing plug which blocks access to a communicating channel 28 leading to the interior of the receptacle 16. By inserting the cannula means into the narrow duct 26 and partially imbedding the cannula tip into the plug 27, accidental discharge of the electrolyte contents is precluded. In addition, the concealment of the cannula means reduces the anxiety customarily experienced by a patient upon seeing a needle. By sealing the inserted tip in the first stage of the injection channel means, the bioelectrode and attached SYRETTE may be conveniently affixed to the patient's skin, without spillage.

With the unfilled bioelectrode attached to the patient, the second stage of the injection channel means 27 is pierced by moving the cannula means through this blocking member to provide an open channel between the SYRETTE cavity 23 and the closed cavity of the bioelectrode 17. By locating the injection channel means 20 along the top surface 12 of the base member 11, the possibility of accidental injection of the cannula means 24 through the base member and into the patient is minimized. Instead, the injection path of needle point is substantially parallel to or away from the skin surface. It is to be realized that numerous methods of developing the general concept of two-stage injection are envisioned, and that the structure disclosed is only illustrative. Likewise, accidental injection of the cannula means can be prevented by adapting the injection channel means to limit cannula means entry by including a blocking shoulder 25.

Electrical operability of the bioelectrode is accomplished by means of an electrode plate 30 disposed within the interior of the receptacle 16. Since a uniform current flow is preferable, the electrode plate may be fixed at an inner surface of the receptacle at a location near point of intersection of the central axis of the base opening 14, when the pouch is suitably deployed. Such placement will also facilitate a parallel orientation between the electrode plate and exposed skin through the opening, further enhancing field uniformity.

The electrode plate may be of stainless steel material and is retained at the interior surface of the receptacle 16 by means of an exterior conductive plate 31, the two plates being spotwelded or otherwise electrically coupled. The external plate 31 is contacted by a wire lead 32 or other coupling means to an external circuit. To prevent fluid leakage between the plates, that portion of the receptacle wall 16 sandwiched between the plates is compressed and operates as an effective seal.

FIGS. 1–4 illustrate the inclusion of a wicking member 34 located at the base opening 14. This may be made of any highly wettable material, such as filter paper. When the bioelectrode is filled with electrolyte, the wicking member is saturated and displaces to develop intimate physical contact at the exposed skin surface. Fluid is therefore dispersed uniformly across the contacted skin area by the capillary action of the wicking member. Not only does this covering provide a more uniform current flow at the skin surface, but it also operates to prevent electrode/skin contact which can cause serious burning. When the wicking member is fixed to the base member and covers the opening thereof, it also helps to avoid spillage of electrolyte upon removal of the bioelectrode.

To further reduce spillage of electrolyte upon electrode removal, an expandable absorbent member 35 may be contained within the receptacle interior. A compressed sheet of sponge-like material having minimal air content may be inserted as shown in FIG. 4. Upon injection of electrolyte, the absorbent character of the material 35 causes expansion, partially filling the receptacle cavity. This material also serves to preclude physical contact between the electrode plate 30 and the exposed skin.

Also illustrated in FIGS. 1–4 is a flexible, pourous shield 36 which is disposed within the interior of the receptacle 16 such that when the electrode is flattened, the shield extends laterally to reduce contact between the inner receptacle walls. Migration sealing effects between contacting plastic surfaces are thereby minimized, facilitating ease of expansion in response to electrolyte fluid.

As an illustration of the use of such a deformable, self-sealing electrode, the following steps of application are provided:

1. A dry-state bioelectrode such as illustrated in FIG. 4 is obtained, in combination with a syringe means or similar reservoir. This may be a SYRETTE 21 as described in the present application, or may simply be a conventional syringe suitable for use at the injection channel means of the electrode.

2. The syringe or SYRETTE 21 is then filled with a desired electrolyte and the cannula tip 24 thereof is inserted in the first stage of the two-stage injection channel means 26. At this point the cannula tip is slightly imbedded in the sealing plug 27 which blocks the flow channel 28.

3. The bioelectrode is then placed on the patient's skin at a treatment site and retained either by an adhesive coating on the bottom surface 13 of the base member or by other suitable means.

4. With the electrode affixed at the skin surface, the cannula is thrust forward, piercing the sealing plug 27 as shown in FIG. 4. The flow channel between the syringe cavity and flattened receptacle is now open, and the fluid is ejected from the SYRETTE cavity 23 into the channel 28, causing the receptacle to extend in accordance with the amount of fluid introduced. 5. When the receptacle is sufficiently full, the syringe means 21 is withdrawn, with the sealing plug 27 closing the flow channel 28.

6. Electrical circuitry coupled to the electrode plate by means of the wire lead 32 is actuated and the treatment or procedure is commenced.

Figure 5:
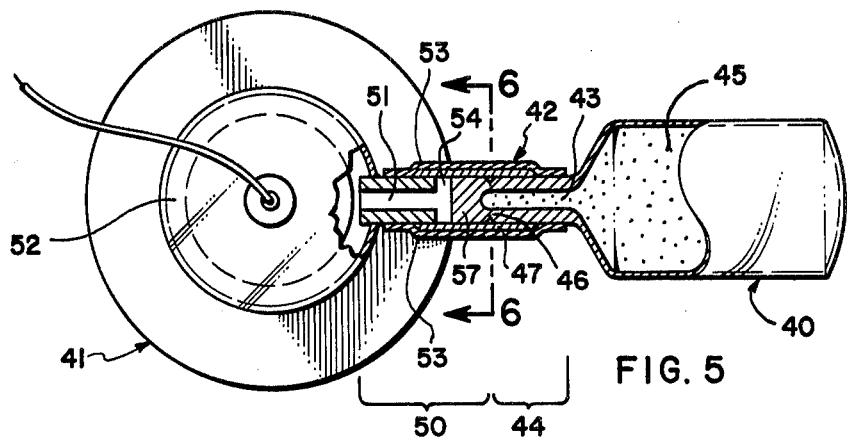
FIG. 5 represents a cut away top view of a self-sealing bioelectrode having an integrally attached reservoir for retaining fluid until fluid transfer to the receptacle is effected.
Figure 6:
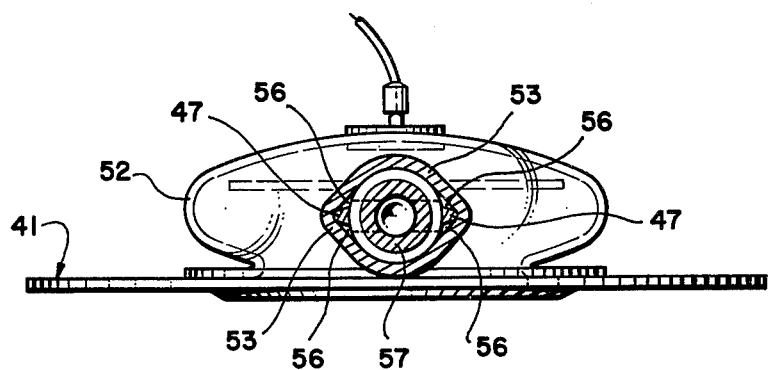
FIG. 6 is a cross sectional view of the electrode-reservoir combination of FIG. 5, taken along line 6—6.
Figure 7:
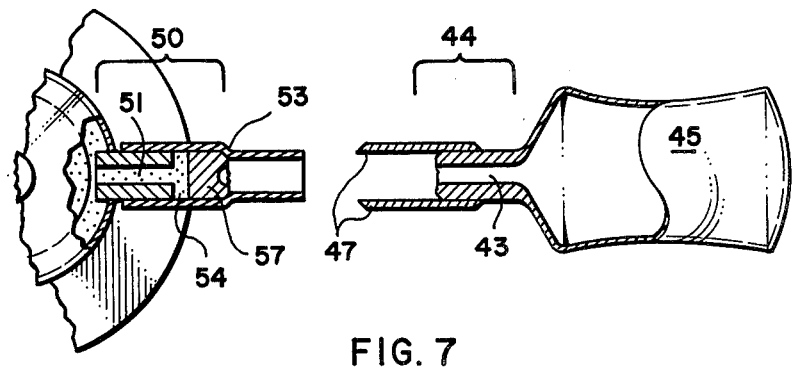
FIG. 7 shows the self-sealing electrode of FIG. 5 after filling of the receptacle and separation of the attached reservoir.

FIGS. 5–7 represent a second embodiment of the self-sealing electrode having a reservoir means 40 integrally attached to the electrode body 41 by self-sealing injection channel means 42. As illustrated, the injection channel means 42 includes an open channel 43 which extends along the reservoir neck 44 from the reservoir cavity 45 to a breakaway connection 46. The reservoir neck has a pair of radially protruding ribs 47 fixed at the outer surface of the neck and extending along the axis of the open channel 43 beyond the breakaway connection 46. The attachment of these ribs is more clearly portrayed in FIGS. 6 and 7.

The electrode channel section 50 of the injection channel means 42 includes a flow channel 51 which communicates from the receptacle cavity 52 through a self-sealing mechanism which connects the open channel 43 and the flow channel 51. FIGS. 5–7 illustrate the use of a tube sealing system for such a mechanism, to permit transfer of fluid to the electrode, while blocking back flow after filling is completed.

Such a configuration includes a tight fitting elastic tube 53 which encloses the reservoir neck 44 and the electrode channel section 51. The electrode channel section 50 has a transverse duct 54 which communicates from the flow channel 51 to lateral surfaces of the electrode channel section 50. The duct openings at the channel section surface are located so as to be proximate to the extending portion of the ribs 47. The enclosing elastic tube is thereby distended by the radially extending ribs, providing a tube flow channel 56 (FIG. 6) along the surface of the channel section to the transverse duct 54 which opens at this surface. A closed terminal section 57 blocks forward flow and provides a site for breakaway attachment of the reservoir neck 44 at the connection point 46. Until broken, this connection 46 operates as a seal to retain the fluid contents within the reservoir 45.

This embodiment of the subject invention is especially useful with dry-state electrodes which are packaged and sold with a particular electrolyte or medicament attached thereto in a separate reservoir, in ready to use form. Under such applications the electrode/reservoir combination would be attached to a patient's skin. When properly positioned, the individual or attendant bends or twists the breakaway connection 46, severing the reservoir neck from the electrode channel section and forming a gap therebetween. The fluid from the reservoir cavity 45 may then be forced down the open channel 43, through the resultant gap 46, down the tube flow channel 56, in the duct opening 54, through the flow channel 51 and into the electrode cavity. When the filling operation is completed, the reservoir and attached ribs are removed from the elastic tube as illustrated in FIG. 7. The elastic tube is then free to seal the duct openings and preclude back flow of the transferred fluid.

It will be apparent that the tube sealing system is just one of numerous ways of implementing the inventive concepts disclosed herein. As specifically referenced in the parent case, a sealed bag can be attached at the flow channel as a reservoir means. A weak seal may be provided between the flow channel and reservoir to retain the fluid within the reservoir during storage. To fill the electrode receptacle, the bag is merely compressed, breaking the seal which otherwise blocks the fluid entry into the flow channel. The bag may thereafter be twisted closed or otherwise sealed at the mouth thereof. In the event that no counter pressure is exerted within the electrode cavity to cause adverse back flow to the reservoir, the voided bag may simply be ignored.

The present invention provides substantial improvement over current bioelectrodes. Because of the dry-state of the electrode, storage may be indefinite without fear of leakage or drying. Ease and convenience of application are substantially improved because electrolyte solutions need not be inserted until the electrode is fully in place on the patient's skin. The person administering the particular treatment or procedure is therefore not confronted with the mess often associated with prefilled electrodes. Likewise, removal of the electrode is less troublesome due to the fluid restraining action of the wicking member. Also significant is the fact that the self-sealing bioelectrode is substantially void of air pockets within the receptacle cavity and therefore establishes a more uniform current flow.

In the flattened electrode configuration, improved electrical contact at the electrode plate is insured inasmuch as fluid contact thereat is maintained by the inflating force of the injected electrolyte. By providing electrode structure which is substantially flattened during storage, affixed to the skin, and then deployed by inflating the receptacle with electrolyte, minimal air intake is ensured and reliability of the procedures is improved.

Although preferred forms of the invention have been herein described, it is to be understood that present disclosures are by way of example and that variations are possible without departing from the scope of the hereinafter claimed subject matter, which subject matter is to be regarded as the invention.

We claim:

1. A self-sealing bioelectrode for use with electrode fluids including:
    (a) a sheet-like base member having a base opening therethrough, and adapted at a bottom surface thereof for conforming contact at a skin surface;
    (b) a receptacle having an opening which is attached at said base member to define a fluid channel through said base opening to the interior of said receptacle;
    (c) an injection channel means communicating between the exterior and interior of said receptacle for filling said receptacle with fluid when affixed at said skin surface, said channel means having restricted access means for passing said fluid into said receptacle while precluding subsequent introduction of other fluids therethrough;
    (d) a conductive electrode plate disposed within said receptacle interior at such location so as to be remote from said base opening when said electrode is filled with fluid; and
    (e) means for coupling said electrode plate to an electric circuit.

2. An electrode as defined in claim 1, wherein said receptacle is constructed of deformable material which adapts said receptacle to be flattened against said base member causing the receptacle to be substantially void of air when in a dry-state, but expandable when filled with fluid after being affixed to said skin surface.

3. An electrode as defined in claim 1, further comprising a reservoir means integrally attached to and having opening means communicating at said injection channel means.

4. An electrode as defined in claim 3, wherein said reservoir means comprises a prefilled bag of electrode fluid having a weak seal as opening means thereof and being operable to break upon squeezing to facilitate discharge of bag contents into the injection channel means.

5. An electrode as defined in claim 3 wherein said restricted access means comprises:
    a. breakaway connection means between the reservoir means and injection channel means which is adapted to break upon bending or twisting to form an opening from said reservoir means to a tube flow channel,
    b. radially protruding rib structure projecting along a length of said breakaway connection means and being attached at the reservoir means,
    c. an enclosing elastic tube attached at said injection channel means and stretched around said breakaway connection means, said tube being partially extended along an intermediate length thereof away from an exterior surface of said channel means by said rib structure to thereby form said tube flow channel between said exterior surface and said elastic tube, and
    d. said opening means communicating from said tube flow channel to said injection channel means.

6. An electrode as defined in claim 1, further comprising a wicking member disposed across said base opening proximate to said bottom surface.

7. An electrode as defined in claim 1, wherein said base member is made of flexible material adaptable for emplacement over sharply contoured skin surfaces.

8. An electrode as defined in claim 1, further comprising an absorbent shield disposed interior of said receptacle between said electrode plate and said base opening and having sufficient size for precluding substantial physical contact between contacting interior surfaces of said receptacle and between said electrode plate and said skin surface.

9. An electrode as defined in claim 1, wherein said injection channel means includes a flow channel communicating between said receptacle interior and an external location.

10. An electrode as defined in claim 9, wherein said restricted access means comprises a self-sealing plug located within said channel and impervious to fluids except as they may be delivered through said plug by an inserted syringe means.

11. An electrode as defined in claim 9, wherein said channel is disposed along the top surface of said base member providing a direction of electrolyte injection substantially parallel to said top surface and away from said skin surface.

12. An electrode as defined in claim 1, further comprising means for two-stage injection of electrolyte, said first stage comprising means for blocking fluid flow from an inserted tip of an electrolyte containing syringe means to facilitate temporary storage in ready-to-charge condition, and a second stage comprising means requiring further movement of said syringe means to enable communication of electrolyte through said tip to said receptacle interior.

13. An electrode as defined in claim 1, wherein said electrode plate has a periphery and surface substantially similar in contour to said base opening for improving uniform electric field at said opening during operation.

14. An electrode as defined in claim 1, wherein said electrode plate coupling means comprises an exterior conductive plate mounted opposite and electrically coupled to said interior plate with a wall section of the receptacle compressed therebetween to seal off fluid flow between said plates, said exterior plate having means for coupling to external electrical circuitry.

15. An electrode as defined in claim 14, wherein said electrical coupling between said interior and exterior plates comprises a spot weld connection.

16. An electrode as defined in claim 1, further comprising a removable SYRETTE coupled to said injection channel means for charging said electrode, said SYRETTE including a closed chamber having a pumping means and a cannula means providing a fluid path between said chamber and an exterior point from said SYRETTE, said cannula means being adapted for mating with a section of said injection channel means to form a continuous channel connecting said chamber with said receptacle interior.

* * * * *